United States Patent [19]

Mezei et al.

[11] 4,382,122

[45] May 3, 1983

[54] CALCIUM ASSAY

[75] Inventors: Louis M. Mezei, Fremont; Laurence N. Jacobs, Sunnyvale; Samuel C. Berry, Hayward, all of Calif.

[73] Assignee: Sherwood Medical Industries Inc., St. Louis, Mo.

[21] Appl. No.: 311,177

[22] Filed: Oct. 14, 1981

[51] Int. Cl.³ ............................................. G01N 33/84
[52] U.S. Cl. ........................................ 436/74; 8/636; 422/61; 436/79; 549/33
[58] Field of Search ............ 23/230 B, 230 R; 8/594, 8/598, 636; 549/33; 422/61; 436/74, 79, 176

[56] References Cited

U.S. PATENT DOCUMENTS

| 3,095,277 | 6/1963 | Free et al. | 23/230 B X |
| 3,310,362 | 3/1967 | Fiess | 8/598 X |
| 3,754,865 | 8/1973 | Gindler | 23/230 B |
| 3,934,977 | 1/1976 | Cleaver | 436/79 X |

OTHER PUBLICATIONS

Chang, Chem. Abstr., vol. 79, 1973, No. 118033x.
Gindler et al., Chem. Abstr., vol. 78, 1973, No. 25984x.

*Primary Examiner*—Arnold Turk
*Attorney, Agent, or Firm*—Wood, Dalton, Phillips, Mason & Rowe

[57] ABSTRACT

The stability of a reagent comprising an aqueous solution of a phenolsulphonephthalein dye is enhanced by the presence of a weak acid in the reagent.

25 Claims, No Drawings

CALCIUM ASSAY

BACKGROUND OF THE INVENTION

1. Field of the Invention

This invention relates to a reagent and method for demonstrating and determining calcium in a liquid sample and, more particularly, this invention relates to means for stabilizing an aqueous solution of methylthymol blue dye, or similar dye, in a reagent useful in assaying calcium in biologic fluids.

2. Brief Description of the Prior Art

Gindler U.S. Pat. No. 3,754,865 (Aug. 28, 1973), the disclosure of which is hereby incorporated by reference, discloses a reagent and method for demonstrating and determining calcium in biologic fluids. According to the Gindler patent, methylthymol blue, or a similar phenolsulphonephthalein dye, present in aqueous solution in a diagnostic reagent binds with calcium in a liquid sample to produce a colored complex, the concentration of which is directly and linearly related to the concentration of calcium in the sample, and which can be readily determined using standard spectrophotometric techniques.

The Gindler patent further discloses that interference from magnesium present in the sample can be eliminated by the presence of a sequestering agent such as 8-quinolinol (8-hydroxyquinoline) which complexes with magnesium, thus preventing magnesium from complexing with the dye.

The preferred reagent of the Gindler patent also includes a micelle-forming protective colloid (which holds lipids in solution, thus preventing turbidity, and eliminates errors due to the presence of protein), a reducing agent (which stabilizes the color of the calcium dye complex) and a buffering agent (which prevents absorption of light by uncomplexed dye). The reagent is effective in assaying calcium even in samples which contain proteins, phosphates and bilirubin.

Methylthymol blue dye, and similar phenolsulphonephthalein dyes, are known to be chemically unstable in aqueous solution. The Gindler patent discloses that this is not the case with respect to acidic solutions of the dye which, preferably, contain a protective colloid and a magnesium complexing agent. Gindler discloses that such aqueous solutions of methylthymol blue can be stabilized for as long as about one year by maintaining the pH of the solution below about 4 by the addition of a strong acid having a water-soluble calcium salt to the solution in an amount sufficient to achieve the desired pH.

This teaching of the Gindler patent is consistent with the theory that phenolsulphonephthalein dye instability is a result of base-catalyzed hydrolysis of amino groups present in the dye molecule.

Practical experience with a commercial form of the reagent described in the Gindler patent has revealed that, even with the presence of strong acids, methylthymol blue dye is somewhat unstable. Such instability contributes to a rise in optical density of blank solutions containing the reagent, and a drop in linearity of the colorimetric reaction. Specifically, rises in blank optical density to greater than about 1.3, followed by drops in linearity of up to 10%, have been experienced.

SUMMARY OF THE INVENTION

It is an object of the present invention to overcome one or more of the problems described above.

According to the present invention, a weak acid is used to stabilize the dye of the diagnostic reagent described in Gindler patent 3,754,865.

Any of a variety of weak acids may be used in the invention, and the pH of the reagent need not necessarily be maintained below 4, but should be less than about 5.5. Sufficient weak acid should be present in the reagent to maintain solubility of any sequestering agent, such as 8-hydroxyquinoline, present in the reagent.

It has been found that substitution of a weak acid for a strong acid in the reagent significantly increases the stability of the dye solution, thus slowing the rate of blank optical density increase by a factor of two to three. Hence, the reagent is ideal for use in automated equipment. Further, shelf life is increased, room temperature storage of the reagent is practical and the performance of the reagent on high quality spectrophotometric equipment is improved.

Thus, the invention provides a diagnostic reagent of enhanced stability, a method of stabilizing an aqueous solution of a phenolsulphonephthalein dye, a method of colorimetrically determining calcium in biologic fluids, and a diagnostic kit including the reagent.

Further objects and advantages of the invention will be apparent from the following detailed description taken in conjunction with the appended claims.

DETAILED DESCRIPTION OF THE INVENTION

The present invention represents an improvement over the reagent and method of Gindler U.S. Pat. No. 3,754,865, and resides in the use of a weak acid as a dye stabilizer in place of the strong acid of the patent.

According to the present invention, and consistent with the disclosure of the Gindler patent, other than in the selection of a stabilizer, a diagnostic reagent for colorimetric determination of calcium comprises an aqueous solution of a selected phenolsulphonephthalein dye and a weakly acidic stabilizer, which solution preferably includes a micelle-forming protective colloid, and a sequestering agent which serves to eliminate interference from magnesium by complexing therewith.

A working reagent containing the dye reagent preferably further includes a buffer and a reducing agent.

The preferred dye for use in this invention is methylthymol blue (preferably the sodium salt thereof). Methylthymol blue is 3,3'-Bis[N,N'-di(carboxymethyl)-aminomethyl]thymolsulfonphthalein, and has the following structure:

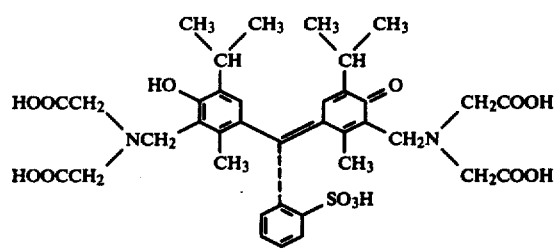

The present invention will be particularly described with respect to the use of methylthymol blue as the reagent dye. However, other phenolsulphonephthaleins containing as substituents on the phenol rings, a methylenenitrilodiacetic acid group in the 6 and 6'-positions can also be used as long as the calcium complex with the reagent dye exhibits a maximum absorbance at a wave length substantially different from that at which bilirubin exhibits a maximum absorbance (about 420 nm). To this end, useful dyes also contain substituents in the 2,2' and 5,5'-positions on the phenol rings. Such substituents serve to shift the maximum absorbance of the calcium dye complex to a wavelength of greater than about 590 m$\mu$. The substituents employed must not themselves be capable of binding calcium.

Useful dyes can be represented as having the following structure:

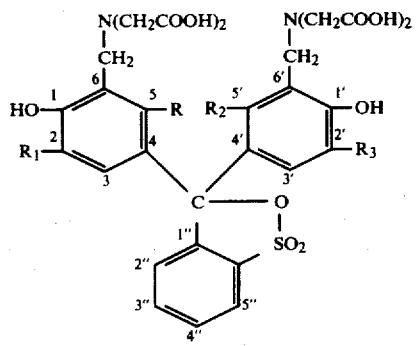

wherein R, $R_1$, $R_2$, and $R_3$ are spectrum shifting, non-calcium binding substituents. They can be individually selected from alkyl groups (e.g., methyl, ethyl, propyl, butyl, hexyl, 2-ethyl-hexyl, decyl, etc.), aryl groups (e.g. phenyl, halogenated phenyls such as chloro and bromo, 1 and 2 naphthyl, toluyl, pyridyl, etc.), halogen atoms (e.g. Cl, Br), and oxygen, sulfur, and/or nitrogen containing groups such as ethers (methoxy, ethoxy), thioethers (methylthio ether), sulfoxide (methyl or phenyl sulfoxide), sulfonamide, and amines [(dimethylamino) amide carboxyl].

Dyes wherein the substituents are lower alkyl groups (e.g. less than about 10 carbon atoms) are thought to be most useful. The most readily available of these are methylthymol blue (R and $R_2$ are CH—, and $R_1$ and $R_3$ are $(CH_3)_2CH$—), and methylxylenol blue (R, $R_1$, $R_2$ and $R_3$ are $CH_3$—).

In addition, one or more of the above substituents may be in the 2", 3", 4" and/or 5" positions of the sulfo carboxylic acid-derived ring. The sulfo carboxylic acid-derived ring may itself be part of a naphthalene or other isocyclic group or may even be heterocyclic, such as pyridine or quinoxaline. It is even possible that in place of the sulfo carboxylic acid-derived ring there may be a linear group derived from 3-sulfo-acrylic acid.

With human blood serum or plasma, the use of about $(2.4 \times 10^{-4})-(4.0 \times 10^{-4})$ millimole of methylthymol blue dye per 50 microliters of biologic fluid is ordinarily sufficient to permit colorimetric analysis. Since the uncomplexed dye strongly absorbs light outside of the pH range of about 10–13, analysis should be accomplished within this range. To this end, a suitable buffer which functions in the pH range of about 10–13 and which does not significantly bind calcium or form precipitates therewith can be used. Examples of useful buffers include alkyl amines such as hydroxyalkyl amines, e.g., monoethanolamine; aliphatic alkyl amines, e.g., diethylamine or triethylamine; aromatic alkyl amines, e.g., benzyl amines such as 2-phenylethylamine; and calcium free conjugate acid-base pairs, e.g. ammonium ion such as from ammonium chloride, ammonium borate, or ammonium acetate and ammonia.

While the method of the present invention employing methylthymol blue dye has the decided advantage of permitting the direct colorimetric analysis of biologic fluids without the necessity for removing phosphates, bilirubin or proteins, it is preferred that, in addition to the dye, a high molecular weight, calcium-free micelle-forming protective colloid also be present during analysis. Several advantages are thought to accompany the use of the colloid.

The colloid can hold lipids in solution and thus prevent interference in the absorption spectrum due to turbidity. In addition to preventing turbidity, it is believed that the use of the protective colloid is also important in eliminating errors due to the presence of proteins in the biologic fluid being analyzed. It is known that proteins can bind with dyes (unmetallized or metallized) and thereby influence the colorimetric spectrum obtained for the fluid.

However, since the determination of calcium concentration is obtained by comparing the observed absorbance of the biologic fluid sample with the observed absorbance of standard protein-free aqueous solutions containing known calcium concentrations, the spectral influence due to a protein-dye complex is not present in the measurement on the standard and this can result in erroneous results. The use of a protective colloid in both the fluid being analyzed and the standard is believed to minimize this potential for error. It appears that the colloid either functions to strongly bind the reagent dye itself and thereby prevent the dye from binding with protein in the biologic fluid sample, or forms a colloid-dye complex in the standard having an absorbance spectrum similar to the protein-dye spectrum present in the biologic fluid.

Useful protective colloids include polyvinylpyrrolidone and nonionic surfactants such as epoxide polymers and copolymers, e.g. polyethylene and polypropylene oxide, or the 9-ethyleneoxide adduct of p-nonylphenol; polyvinyl alcohols; carbohydrate polymers; betaines; and high molecular weight anionic and cationic surfactants and polymers such as sodium dodecyl sulphate and hexadecyl trimethyl ammonium chloride or bromide, as well as mixtures thereof. Based on about 50 microliters of biologic fluid, about 4.5–13.5 milligrams of protective colloid are desirably employed.

Further examples of suitable colloids are given in Gindler U.S. Pat. No. 3,754,865 (Aug. 28, 1973), the disclosure of which is incorporated herein by reference.

It is necessary that magnesium either be removed from the sample fluid prior to analysis, or complexed in a manner which prevents it from complexing with the dye. 8-Quinolinol (8-hydroxyquinoline) is a suitable complexing agent which can be used. Due to the exceptionally strong calcium binding power of methylthymol blue, 8-hydroxyquinoline can be used in concentrations sufficient to effectively tie up the magnesium present in the sample without a risk of drawing calcium away from the dye. With human blood serum or plasma, about $3.5 \times 10^{-2} - 11.2 \times 10^{-2}$, and preferably at least about $5 \times 10^{-2}$, millimole of the complexing agent per 50 microliters of biologic fluid sample can be used.

A reducing agent is desirably included in the biologic fluid to be analyzed in order to stabilize the color of the calcium-dye complex. Useful reducing agents are those which function as antioxidants and include, for example, sodium sulfite and salts of hydroxylamine, such as hydroxylammonium chloride. In order to effect color stabilization for extended periods (e.g. several hours or more), a molar excess of the reducing agent, based on the dye, of at least several hundred times, and preferably at least about 500 times, should be used. The use of such large excesses also results in substantially the same ionic environment being present in the sample to be analyzed and in the standard solution used for calibration. In this manner, any potentially disturbing effects from the ionic environment in the biologic fluid, such as due to the presence of proteins, are eliminated.

Although the colorimetric reaction is carried out at a relatively high pH, it is known that aqueous solutions of methylthymol blue are relatively unstable, and this instability is believed to be the result of base-catalyzed hydrolysis of amino groups present in the dye molecule.

To the end of stabilizing the dye in a dye reagent, Gindler U.S. Pat. No. 3,754,865 teaches that aqueous solutions of methylthymol blue can be stabilized for as long as about one year by maintaining the pH of the dye reagent solution below about 4, and that such pH maintenance can be accomplished by simple addition of a strong acid having a water-soluble calcium salt to an aqueous solution of methylthymol blue and other ingredients present in the dye reagent in an amount sufficient to achieve the indicated pH.

It has been found in practice, however, that methylthymol blue solutions, even with the presence of a strong acid, exhibit only limited stability, sometimes resulting in an increase in the optical density of blank solutions (e.g. over 1.3 OD) followed by a decrease in the linearity of the colorimetric reaction (e.g. greater than about 10% decrease). Such instability problems may make a reagent unacceptable for use in many laboratories.

According to this invention, therefore, it has been found that the use of a weak acid as a stabilizing component in a dye reagent in place of a strong acid provides enhanced stability, thus effecting significant slowing of blank optical density increases, maintenance of linearity, and provision of a longer shelf life for the reagent.

This result is especially surprising in view of the teaching of Gindler U.S. Pat. No. 3,754,865 that the pH of the dye reagent should be maintained at less than about 4.0 by the presence of a strong acid, and the widely held belief that methylthymol blue dye instability is the result of a base-catalyzed hydrolysis. The term "weak acid" is used herein in its conventional sense, and generally includes those acids having a pKa greater than about 2.0.

Usable weak acids include, without limitation, propionic acid, acetic acid, benzoic acid, phthalic acid and formic acid. O-phthalic acid is preferred.

According to the invention, it is not necessary that the pH of the reagent dye solution be maintained below about 4.0, but the pH should not be greater than about 5.5, at which point base-catalyzed hydrolysis of the dye, and precipitation of 8-quinolinol may be encountered. Preferably, the pH will be maintained below about 4.5, and can be less than 4.0, depending on the acid used.

In the preferred embodiment of Gindler U.S. Pat. No. 3,754,865, 8-quinolinol (8-hydroxyquinoline) is included in the reagent in an amount sufficient to complex with magnesium found in a liquid sample to be mixed with the reagent. The solubility of 8-hydroxyquinoline increases with decreasing pH; therefore, it is necessary that the weak acid be present in the reagent in an amount sufficient to maintain the 8-hydroxyquinoline in solution. Thus, the pH need not be maintained at any point lower than that required to both render 8-hydroxyquinoline in the reagent soluble, and to stabilize the dye. Thus, the concentration of a specific weak acid in the reagent may be readily empirically determined.

The following specific examples will serve to illustrate the practice of the invention. However, no unnecessary limitations should be implied therefrom, since modifications within the scope of the invention will be obvious to those skilled in the art.

EXAMPLES

EXAMPLE 1

In the reagent dye solution, useful concentration ranges of components other than the weak acid are as follows (based on one liter of solution):

| | |
|---|---|
| methylthymol blue (sodium salt) | 0.05–1.25 mmole |
| polyvinyl pyrrolidone | 3–9 gm |
| 8-hydroxyquinoline | 23–75 mmoles |

A solution useful as a dye reagent acid has the following composition (based on one liter of solution):
  3.4 gm o-phthalic acid
  6.0 gm polyvinyl pyrrolidone
  0.160 gm methylthymol blue dye
  3.6 gm 8-hydroxyquinoline
  Balance distilled water.

The foregoing dye solution has a pH of about 4.1, and may be mixed in equal volumes with a base solution comprising between about 0.15–0.25 mole of sodium sulfite (buffer), and 2.8–4.2 moles of monoethanolamine (reducing agent) per liter of base solution.

Comparable dye solutions using different weak acids may be obtained by use of the acid in an amount sufficient to obtain the indicated pH, as follows:

| | |
|---|---|
| propionic acid | pH 4.2 |
| acetic acid | pH 4.2 |
| benzoic acid | pH 4.1 |
| formic acid | pH 3.0 |

EXAMPLE 2

A formic acid reagent dye solution, according to Example 1, was prepared and the stability thereof was compared to a dye solution containing HCl made in accordance with the example at Col. 5 of Gindler U.S. Pat. No. 3,754,865. To confirm the fact that the presence of a weak acid as opposed to mere pH control accounts for enhanced stability, the pH of the Gindler HCl reagent was brought to 3.2 by addition of hydrochloric acid. No stability increase was obtained. On the other hand, a dye solution according to the invention using formic acid and a pH of 3.0 resulted in a blank increase equal to only 50% of the blank increase exhibited by the Gindler reagent.

As indicated, the method of the present invention can be simply practiced by independently adding methylthymol blue dye and the other indicated ingredients to a sample of biologic fluid and thereafter colorimetrically analyzing the sample. In order to avoid inducement of protein precipitation by the added reagents, water is desirably also added to the sample. The added water should preferably be at least about 40 times, by volume, the amount of biologic fluid sample used.

While the present method can be accomplished by direct addition of reagents as above indicated, the customary procedure employed by hospitals and the like is to use preformulated, generally aqueous, solutions of the reagent dye and the other desired ingredients. The preformulated compositions are generally referred to as "diagnostic kits" and are sold by a number of chemical supply companies. The principal advantage of "diagnostic kits" is that laboratory workers such as hospital laboratory personnel need not be concerned with separately adding the various necessary ingredients in their proper amounts to the samples to be analyzed. The use of "diagnostic kits" speeds the analytical process and reduces the chances of obtaining incorrect results based on, for example, the use of contaminated or improper ingredients.

In commercial practice, the reagent is best packaged in a diagnostic kit containing two separate preformulated aqueous solutions. One composition (the dye solution) preferably contains an aqueous solution of a dye, a nonionic protective colloid, a magnesium complexing agent, and sufficient weak acid to stabilize the dye. The other composition, referred to as the base solution, contains an aqueous solution of a buffer and a reducing agent.

In practice, substantially equal volumes (generally about 240 milliliters each) of the dye and base solutions are mixed to form a working reagent together prior to making the desired colorimetric calcium determination. About 3 milliliters of the working reagent are used per 50 microliters of biologic fluid sample. Absorbance is read at about 612 nm wave length using well known colorimetric or spectrophotometric techniques.

A calibration graph can be used to determine the actual concentration of calcium. The graph can be prepared from colorimetric determinations on standard aqueous solutions (50 microliters) containing known calcium concentrations (from 0 to about 25 milligrams of calcium per 100 milliliters of solution) to which 3 milliliters of the working reagent have been added.

As indicated above, the possibility of erroneous measurements due to the presence of protein in the sample, which protein is not present in the standard, or due to ionic strength differences between the sample and standard is substantially eliminated by the technique described herein. It has been found that the present method follows Beer's law up to a calcium concentration of at least about 12.5 milligrams per 100 milliliters of sample.

The foregoing detailed description is for clearness of understanding only and no unnecessary limitations should be understood therefrom, as modifications within the scope of the invention will be obvious to those skilled in the art.

We claim:

1. In a reagent comprising an aqueous solution of a dye which comprises a phenolsulphonephthalein dye which contains methylenenitrilo diacetic acid group substituents in the 6 and 6'-positions on the phenol rings and spectrum shifting, noncalcium binding substituents in the 2, 2' and 5, 5'-positions thereof, the improvement wherein said reagent includes a stabilizing amount of a weak acid.

2. The improvement of claim 1 wherein said weak acid is selected from the group consisting of propionic acid, acetic acid, benzoic acid, phthalic acid and formic acid.

3. The improvement of claim 2 wherein said dye is methylthymol blue.

4. In a reagent for determination and demonstration of calcium in a liquid sample, said reagent comprising an aqueous solution of methylthymol blue dye and an amount of 8-hydroxyquinoline sufficient to sequester magnesium present in said sample, the improvement wherein said reagent further includes a weak acid in an amount sufficient to maintain said 8-hydroxyquinoline in solution and to stabilize said methylthymol blue dye, said reagent being substantially free of strong acids.

5. The improvement of claim 4 wherein said weak acid is selected from the group consisting of propionic acid, acetic acid, benzoic acid, phthalic acid and formic acid.

6. The improvement of claim 5 wherein said weak acid is o-phthalic acid and is present in an amount such that the pH of said reagent is less than about 4.5.

7. A method of stabilizing an aqueous solution of a dye which comprises phenolsulphonephthalein dye which contains methylenenitrilo diacetic acid group substituents in the 6 and 6'-positions on the phenol rings and spectrum shifting, noncalcium binding substituents in the 2, 2' and 5, 5'-positions thereof, said method comprising the step of including a dye-stabilizing amount of a weak acid in said dye solution.

8. The method of claim 7 wherein said weak acid is selected from the group consisting of propionic acid, acetic acid, benzoic acid, phthalic acid and formic acid.

9. The method of claim 8 wherein said dye is methylthymol blue.

10. A method of stabilizing an aqueous solution of methylthymol blue dye and 8-hydroxyquinoline, said method comprising the step of including in said solution an amount of a weak acid sufficient to maintain said 8-hydroxyquinoline in solution and to stabilize said methylthymol blue dye, said solution being substantially free of strong acids.

11. The method of claim 10 wherein said weak acid is selected from the group consisting of propionic acid, acetic acid, benzoic acid, phthalic acid and formic acid.

12. The method of claim 10 wherein said weak acid is o-phthalic acid and said acid is present in an amount such that the pH of said solution is less than about 4.5.

13. A reagent comprising an aqueous solution of:
(a) a dye comprising phenolsulphonephthalein dye which contains methylenenitrilo diacetic acid group substituents in the 6 and 6'-positions on the phenol rings and spectrum shifting, noncalcium binding substituents in the 2, 2' and 5, 5'-positions thereof; and
(b) a dye-stabilizing amount of a weak acid.

14. The reagent of claim 13 wherein said weak acid is selected from the group consisting of propionic acid, acetic acid, benzoic acid, phthalic acid and formic acid.

15. The reagent of claim 14 wherein said dye is methylthymol blue.

16. A reagent comprising an aqueous solution of methylthymol blue dye, 8-hydroxyquinoline, and an amount of a weak acid sufficient to maintain said 8-hydroxyquinoline in solution and stabilize said methylthymol blue dye, said solution being substantially free of strong acids.

17. The reagent of claim 16 wherein said weak acid is selected from the group consisting of propionic acid, acetic acid, benzoic acid, phthalic acid and formic acid.

18. The reagent of claim 17 wherein said weak acid is o-phthalic acid and is present in an amount such that the pH of said reagent is less than about 4.5.

19. A diagnostic kit comprising a prepackaged container of the reagent of claim 13 or claim 16.

20. A method of determining calcium in a liquid sample, said method comprising the steps of:
(a) mixing said sample with a reagent comprising an aqueous solution of a phenolsulphonephthalein dye which contains methylenenitrilo diacetic acid group substituents in the 6 and 6'-positions on the phenol rings and spectrum shifting, noncalcium binding substituents in the 2, 2' and 5, 5'-positions thereof, and a dye stabilizing amount of a weak acid, to form a reaction mixture;
(b) observing the color change of said reaction mixture; and
(c) comparing said color change to calibration means.

21. The method of claim 20 wherein said weak acid is selected from the group consisting of propionic acid, acetic acid, benzoic acid, phthalic acid and formic acid.

22. The method of claim 21 wherein said dye is methylthymol blue.

23. A method of determining calcium in a liquid sample, said method comprising the steps of:
(a) mixing said sample with a reagent comprising an aqueous solution of methylthymol blue dye, 8-hydroxyquinoline, and an amount of a weak acid sufficient to maintain said 8-hydroxyquinoline in solution and stabilize said methylthymol blue dye to form a reaction mixture, said solution being substantially free of strong acids;
(b) observing the color change of said reaction mixture; and,
(c) comparing said color change to calibration means.

24. The method of claim 23 wherein said weak acid is selected from the group consisting of propionic acid, acetic acid, benzoic acid, phthalic acid and formic acid.

25. The method of claim 24 wherein said weak acid is o-phthalic acid and is present in an amount such that the pH of said reagent is less than about 4.5.

* * * * *